United States Patent [19]

Carlsson et al.

[11] 4,161,542
[45] Jul. 17, 1979

[54] HEART ACTIVE COMPOUNDS

[75] Inventors: Enar I. Carlsson, Västra Frölunda; Gustav B. R. Samuelsson, Mölnlycke; Bo T. Lundgren, Frillesås, all of Sweden

[73] Assignee: Aktiebolaget Hassle, Goteborg, Sweden

[21] Appl. No.: 864,514

[22] Filed: Dec. 27, 1977

Related U.S. Application Data

[63] Continuation-in-part of Ser. No. 821,956, Aug. 4, 1977, abandoned, which is a continuation of Ser. No. 610,399, Sep. 4, 1975, abandoned.

[30] Foreign Application Priority Data

Jun. 4, 1975 [SE] Sweden ..................... 7506348

[51] Int. Cl.² .................... A61K 31/135; C07C 93/06; C07C 87/29; C07C 43/20
[52] U.S. Cl. .................... 424/330; 260/570.7; 260/570.8 R
[58] Field of Search .................... 424/330; 260/570.7, 260/570.8, 612 D

[56] References Cited

U.S. PATENT DOCUMENTS

| | | | |
|---|---|---|---|
| 3,542,872 | 11/1970 | Koppe et al. | 424/330 |
| 3,843,725 | 11/1974 | Pinhas | 424/330 |
| 3,852,468 | 12/1974 | Howe et al. | 424/330 |
| 3,873,620 | 3/1975 | Pinhas | 424/330 |
| 3,892,799 | 7/1975 | Pinhas | 424/330 |
| 3,929,856 | 12/1975 | Holmes et al. | 424/330 |
| 3,979,456 | 9/1976 | Pinhas | 424/330 |
| 4,067,904 | 1/1978 | Comer et al. | 424/330 |

FOREIGN PATENT DOCUMENTS 2042344 12/1971 France.

Primary Examiner—Albert T. Meyers
Assistant Examiner—D. W. Robinson
Attorney, Agent, or Firm—Brumbaugh, Graves, Donohue & Raymond

[57] ABSTRACT

Amines of the formula I

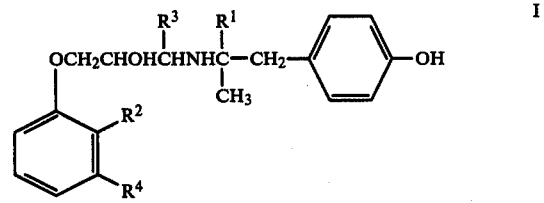

method of preparing the same and pharmaceutical compositions and methods for treating cardiovascular disorders by blocking the β-receptors of the heart in combination with a peripheral vasodilating activity.

74 Claims, No Drawings

HEART ACTIVE COMPOUNDS

This application is a continuation-in-part of our application Ser. No. 821,956 filed Aug. 4, 1977, now abandoned, which, in turn, was a streamlined continuation of application Ser. No. 610,399 of Sept. 4, 1975, now abandoned.

The present invention relates to new potent β-receptor blocking compounds as well as their preparation and a method for treating symptoms and signs of cardiovascular disorders by blocking the β-receptors of the heart by administering to mammals, including man, these new compounds.

The new compounds are those of the general formula

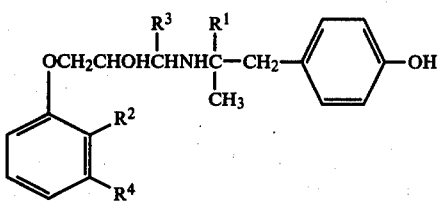

wherein $R^1$ is selected from the group consisting of hydrogen and methyl, $R^2$ is selected from the group consisting of hydrogen, methyl, ethyl, propyl, allyl, methoxy and propargyloxy, $R^3$ is selected from the group consisting of hydrogen, methyl and ethyl, and $R^4$ is selected from the group consisting of hydrogen, and methyl provided that $R^2$ and $R^4$ are not both hydrogen.

The new compounds have valuable pharmacological properties. They block α and β-receptors and have a hypotensive effect in the treatment of cardiovascular diseases. For example, the new compounds can be used in the treatment of arrhythmias, angina pectoris and hypertension. The new compounds also show peripheral vasodilation, believed to be related to the α-receptor blockade and β-receptor mimetic activity of the compounds, which is especially valuable for the last two mentioned indications. One may also use them as intermediates in the preparation of other valuable pharmacological compounds.

Preferred compounds of the present invention are those in which $R^2$ is methyl, ethyl, propyl, allyl, methoxy or propargyloxy and, more specifically, in which $R^2$ is methyl, ethyl, allyl or propargyloxy. The preferred $R^3$ is hydrogen or methyl, and the preferred $R^4$ is hydrogen.

Compounds according to the present invention are:

3-[2-(4-hydroxyphenyl)-1-methylethylamino]-1-o-methylphenoxy-propanol-2;

3-[2-(4-hydroxyphenyl)-1-methylethylamino]-1-o-ethylphenoxy-propanol-2;

3-[2-(4-hydroxyphenyl)-1-methylethylamino]-1-o-propylphenoxy-propanol-2;

3-[2-(4-hydroxyphenyl)-1-methylethylamino]-1-o-allylphenoxy-propanol-2;

3-[2-(4-hydroxyphenyl)-1-methylethylamino]-1-o-propargyloxyphenoxy-propanol-2;

3-[2-(4-hydroxyphenyl)-1,1-dimethylethylamino]-1-o-methylphenoxy-propanol-2;

3-[2-(4-hydroxyphenyl)-1,1-dimethylethylamino]-1-o-ethylphenoxy-propanol-2;

3-[2-(4-hydroxyphenyl)-1,1-dimethylethylamino]-1-o-propylphenoxy-propanol-2;

3-[2-(4-hydroxyphenyl)-1,1-dimethylethylamino]-1-o-allylphenoxy-propanol-2;

3-[2-(4-hydroxyphenyl)-1,1-dimethylethylamino]-1-o-propargyloxyphenoxy-propanol-2;

3-ethyl-3-[2-(4-hydroxyphenyl)-1-methylethylamino]-1-o-allylphenoxy-propanol-2;

3-[2-(4-hydroxyphenyl)-1-methylethylamino]-1-[2,3-dimethylphenoxy]-propanol-2;

3-[2-(4-hydroxyphenyl)-1-methylethylamino]-1-o-methoxyphenoxy-propanol-2;

3-methyl-3-[2-(4-hydroxyphenyl)-1-methylethylamino]-1-o-ethylphenoxy-propanol-2;

3-methyl-3-[2-(4-hydroxyphenyl)-1,1-dimethylethylamino]-1-o-methylphenoxy-propanol-2;

3-methyl-3-[2-(4-hydroxyphenyl)-1,1-dimethylethylamino]-1-o-allylphenoxy-propanol-2; and 3-[2-(4-hydroxyphenyl)-1-methylethylamino]-1-m-methylphenoxy-propanol-2.

Salt forming acids may be used in preparing therapeutically acceptable salts of the compounds. These are: hydrohalogen acids, sulfuric acid, phosphoric acid, nitric acid, perchloric acid, aliphatic, alicyclic, aromatic or heterocyclic carboxy or sulfonic acids such as formic, acetic, propionic, succinic, glycolic, lactic, malic, tartaric, citric, ascorbic, maleic, hydroxymaleic, or pyruvic acid, phenylacetic, benzoic, p-aminobenzoic, anthranilic, p-hydroxybenzoic, salicyclic or p-aminosalicyclic acid, embonic acid, methanesulfonic, ethanesulfonic, hydroxyethane sulfonic, ethylenesulfonic, halogenbenzenesulfonic, toluenesulfonic, naphthylsulfonic, or sulfanilic acid, methionine, tryptophane, lysine or arginine.

The substances are intended to be administered orally or parenterally for acute and chronic treatment of the above-mentioned cardiovascular disorders.

The biological effects of the new compounds have been tested, and the different tests carried out will be shown and explained below.

The new compounds are obtained according to methods known per se. Thus, a compound of formula II

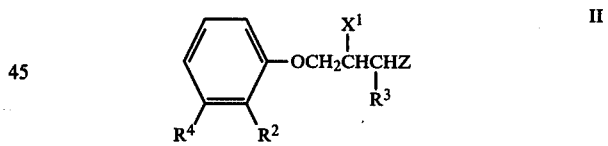

wherein $R^2$, $R^3$ and $R^4$ have the meaning given above, $X^1$ is a hydroxy group, Z is a reactive, esterified hydroxy group, or $X^1$ and Z together form an epoxy group, is reacted with an amine of the formula

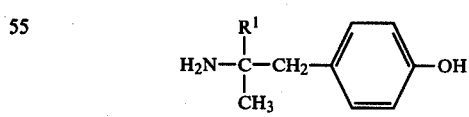

wherein $R^1$ has the same meaning as given above.

A reactive, esterified hydroxy group is particularly a hydroxy group esterified with a strong, inorganic or organic acid, preferably a hydrohalogen acid, such as hydrochloric acid, hydrobromic acid, or hydroiodic acid, further sulfuric acid or a strong organic sulfonic acid, e.g., benzenesulfonic acid, 4-bromobenzenesulfonic acid, or 4-toluenesulfonic acid. Thus, Z is preferably chloro- bromo or iodo.

This reaction is carried out in a common way. When using a reactive ester as a starting material the preparation takes place preferably in the presence of a basic condensing agent and/or with an excess of an amine. Suitable basic condensing agents are, e.g., alkali metal hydroxides such as sodium or potassium hydroxide, alkali metal carbonates such as potassium carbonate and alkali metal alcoholates such as sodium methylate, potassium ethylate or potassium tert.-butylate.

Further, a compound of formula III

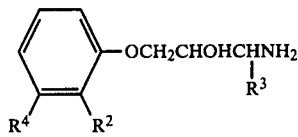

III wherein $R^2$, $R^3$ and $R^4$ have the meanings given above is reacted with a compound of the formula

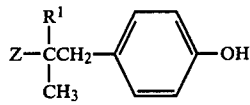

wherein $R^1$ and Z have the same meanings as given above.

This reaction is carried out in a common way, preferably in the presence of a basic condensing agent and/or an excess of an amine. Suitable basic condensing agents are, e.g., alkaline alcoholates, preferably sodium or potassium alcoholate, or also alkaline carbonates such as sodium or potassium carbonate.

Further a compound of formula IV

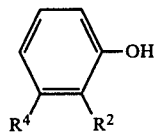

IV wherein $R^2$ and $R^4$ have the same meanings as given above is reacted with a compound of formula V

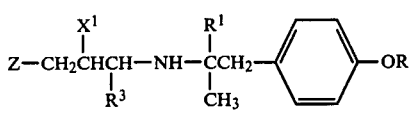

V wherein Z, $X^1$ and $R^1$ and $R^3$ have the same meanings as given above and R is a splittable, protecting group.

This reaction is carried out in a common way. In those cases where reactive esters are used as starting material, the compound of formula IV may suitably be used in the form of its metal phenolate such as alkali metal phenolate, preferably sodium phenolate, or one works in the presence of an acid binding agent, preferably a condensing agent, which can form a salt of the compound of formula IV as an alkali metal alcoholate.

Further, a compound of formula IV

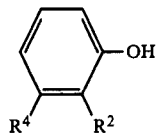

IV wherein $R^2$ and $R^4$ have the same meanings as given above, is reacted with a compound of formula VI

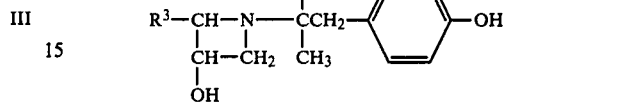

VI wherein $R^1$ and $R^3$ have the same meanings as given above.

This reaction is carried out in a common way. Thus, the reaction is carried out under alkaline conditions in a suitable solvent, such as benzyl alcohol by boiling the reaction mixture for some hours. Thereby the phenol is primarily converted to its metal phenolate such as alkali metal phenolate before it is added to the acetidinol of formula VI.

Further, one may split off a residue from a compound of formula I above, in which the nitrogen atom of the amino group and/or the hydroxy groups have attached thereto a splittable residue.

Such splittable residues are especially those which are splittable by solvolysis, reduction, pyrolysis or fermentation.

Residues splittable by solvolysis are preferably residues splittable by hydrolysis or ammonolysis.

Residues splittable by means of hydrolysis are, e.g., an acyl residue, which, when present, may have functionally varied residues, e.g., oxycarbonyl residues, such as alkoxycarbonyl residues, e.g., tert.-butoxycarbonyl residue, or ethoxycarbonyl residue, aralkoxycarbonyl residues such as phenylloweralkoxycarbonyl residues, e.g., a carbobenzyloxy residue, halogencarbonyl residue, e.g., a chlorocarbon residue, further arylsulphonyl residues such as toluenesulfonyl or bromobenzenesulfonyl residues and possibly as halogenated, such as fluorinated loweralkanoyl residues such as formyl-, acetyl- or trifluoro-acetyl residue or a benzyl residue or cyano group, or silyl residues, such as a trimethylsilyl residue.

Of the above mentioned residues present at the position of the hydroxy groups which residues are splittable by hydrolysis, preferably the oxycarbonyl residues and the loweralkanoyl residues or the benzoyl residues are used.

Besides the above mentioned, also double-bonded residues, which are splittable at the amino group by hydrolysis are used, e.g., alkylidene or benzylidene residue or a phosphorylidene group such as a triphenylphosphorylidene group, whereby the nitrogen atom then obtains a positive charge.

Residues splittable at the hydroxy group and the amino group by hydrolysis are furthermore divalent residues such as substituted methylene. As substituents on the methylene residues any organic residue may be used, whereby it does not matter in the hydrolysis which compound is the substituent to the methylene residue. As methylene substituents, e.g., aliphatic or aromatic residues such as alkyl as mentioned above, aryl, e.g., phenyl or pyridyl may be used. The hydrolysis may be carried out in any common way, suitably in a basic or preferably in an acid medium.

Compounds having residues which are splittable by hydrolysis may also have the formula:

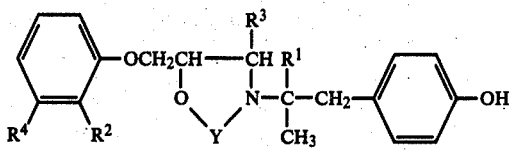

wherein $R^1$, $R^2$, $R^3$ and $R^4$ have the same meanings as given above and Y is a carbonyl or thiocarbonyl residue.

The hydrolysis is carried out in a conventional way, e.g., in the presence of a hydrolyzing agent, e.g., in the presence of an acidic agent such as, e.g., diluted mineral acids such as sulfuric acid or hydrohalogen acid, or in the presence of basic agents such as, e.g., alkali metal hydroxides such as sodium hydroxide. Oxycarbonyl residues, aryl sulfonyl residues and cyano groups may in a suitable way be split off by means of acidic agents as by means of a hydrohalogen acid, suitably hydrobromic acid. Preferably the splitting may take place using diluted hydrobromic acid, possibly in a mixture with acetic acid. Cyano groups are preferably split off by means of hydrobromic acid at an elevated temperature, as in boiling hydrobromic acid, according to the "bromocyano method" (v. Braun). Further, e.g., a tert.-butoxycarbonyl residue may be split off under anhydrous conditions by means of a treatment with a suitable acid, such as trifluoracetic acid. Acidic agents are preferably used in the hydrolysis of compounds of formula VI.

Residues splittable by ammonolysis are especially the halogencarbonyl residues such as the chlorocarbonyl residue. The ammonolysis may be carried out in a common way, e.g., by means of an amine containing at least one hydrogen atom bonded to the nitrogen atom, such as a mono- or diloweralkylamine, e.g., methylamine or dimethylamine, or especially ammonia, preferably at an elevated temperature. Instead of ammonia one may use an agent which gives ammonia such as hexamethylene tetraamine.

Residues splittable by means of reduction are, e.g., an α-aryl-alkyl residue, such as a benzyl residue or an α-aralkoxycarbonyl residue such as a benzyloxycarbonyl residue, which in a common way may be split off by means of hydrogenolysis, especially by catalytically activated hydrogen, as by hydrogen in the presence of hydrogenating catalysts, e.g., Raney-nickel. Further residues splittable by means of hydrogenolysis are 2-halogenalkoxycarbonyl residues such as 2,2,2-trichloroethoxycarbonyl residues or 2-iodoethoxy- or 2,2,2-tribromo-ethoxycarbonyl residues, which may be split off in a common way, suitably by means of a metallic reduction (so-called nascent hydrogen). Nascent hydrogen may be obtained by the influence of metal or metal alloys, such as amalgam on compounds which give hydrogen such as carboxy acids, alcohols or water, whereby especially zinc or zinc alloys together with acetic acid may be used. Hydrogenolysis of 2-halogenalkoxycarbonyl residues may further take place using chromium or chromium (II) compounds such as chromium (II) chloride or chromium (II) acetate.

A residue splittable by reduction may also be an arylsulfonyl group such as a toluenesulfonyl group, which in a common way may be split off by reduction using nascent hydrogen, e.g., by means of an alkali metal, such as lithium or sodium in liquid ammonia, and suitably may be split off from a nitrogen atom. In the reduction one has to take care that other reducible groups are not influenced.

Residues splittable by means of pyrolysis, especially residues splittable from the nitrogen atom, are for example ,suitably substituted or unsubstituted carbamoyl groups. Suitable substituents are, e.g., loweralkyl or arylloweralkyl such as methyl or benzyl or aryl, as phenyl. The pyrolysis is carried out in a common way, whereby one may have to take care of other thermally susceptible groups.

Residues splittable by means of fermentation, especially residues splittable from the nitrogen atom are, for example, suitably substituted or unsubstituted carbamoyl groups. Suitable substituents are, e.g., loweralkyl or arylloweralkyl, such as methyl or benzyl, or aryl such as phenyl. The fermentation is carried out in a common way, e.g., by means of the enzyme urease or soybean extract at about 20° C. or slightly elevated temperature.

Further, a Schiff's base of formula VIII or IX

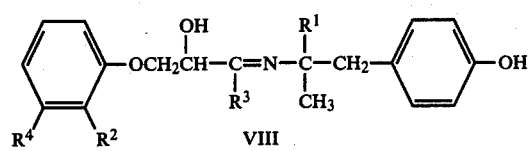

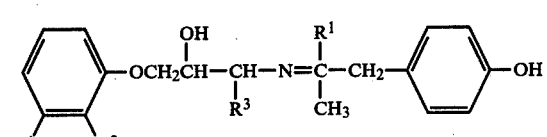

or a cyclic tautomer corresponding to formula IX of formula X

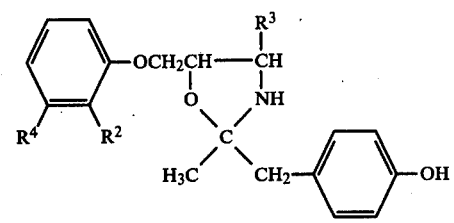

can be reduced, wherein $R^1$, $R^2$, $R^3$ and $R^4$ have the same meanings as given above, $R^1$ not being methyl and wherein the compounds of formula IX and X may exist together, too. This reduction is carried out in a common way, e.g., using a di-light metal hydride such as sodium-borohydride, lithium aluminum hydride, using a hydride such as Boran with formic acid, or by means of a catalytic hydrogenation, as with hydrogen in the presence of Raney-nickel. In the reduction one has to take care that other groups are not affected.

Further, the oxo group in the compound of formula XI

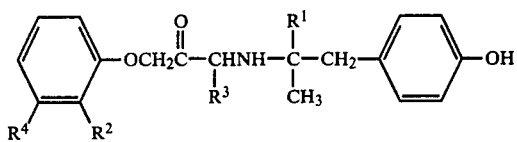

wherein $R^1$, $R^2$, $R^3$ and $R^4$ have the same meanings as given above, can be reduced to a hydroxy group. This reduction is carried out in a common way, especially using a di-light metal hydride as mentioned above, or according to the "Meerwein-Pondorf-Verley method" or a modification thereof, suitably using an alkanol as a reaction component and as solvent, such as isopropanol, and using a metal alkanolate, such as metal isopropanolate, e.g., aluminum isopropanolate.

Further, in a compound of formula XII

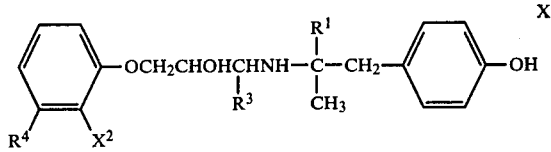

wherein $R^1$, $R^3$ and $R^4$ have the same meanings as given above, and wherein $X^2$ is a residue, which is able to be transformed to a residue $R^2$ one transforms $X^2$ to $R^2$.

Further, the oxo group in a compound corresponding to formula I and which carries an oxo group at a carbon atom bound to a nitrogen atom may be reduced to two hydrogen atoms.

Said compounds are, e.g., such of the formula XIII

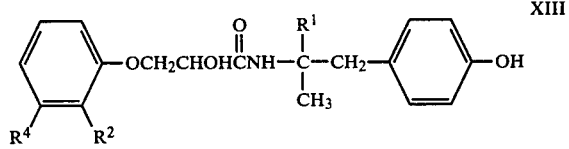

wherein $R^1$, $R^2$ and $R^4$ have the meaning as given above, and $R^3$ is hydrogen.

The reduction can be carried out according to the above described manner using complex metal hydrides, e.g., lithium aluminum hydride or di-isobutylaluminiumhydride. Suitably the reaction takes place in an inert solvent such as an ether, e.g., diethylether or tetrahydrofuran.

In a common way the substituents may be varied from the compounds obtained within the end product as well as the compounds obtained may be introduced, split off or transformed into other end products.

Depending on the process conditions and the starting material, the end product is obtained either in free form or in the form of its acid addition salt, which is included in the scope of the invention. Thus, for example, basic, neutral or mixed salts may be obtained as well as hemiamino, sesqui- or polyhydrates. The acid addition salts of the new compounds may in a manner known per se be transformed into free compounds using, e.g., basic agents such as alkali or ion exchange. On the other hand, the free bases obtained may form salts with organic or inorganic acids. In the preparation of acid addition salts preferably such acids are used which form suitable therapeutically acceptable salts. Such acids are, e.g., hydrohalogen acids, sulfuric acid, phosphoric acid, nitric acid, perchloric acid, aliphatic, alicyclic, aromatic or heterocyclic carboxy or sulfonic acids, such as formic, acetic, propionic, succinic, glycolic, lactic, malic, tartaric, citric, ascorbic, maleic, hydroxymaleic or pyruvic acid, phenylacetic, benzoic, p-aminobenzoic, anthranilic, p-hydroxybenzoic, salicylic or p-aminosalicylic acid, embonic acid, methanesulfonic, ethanesulfonic, hydroxyethanesulfonic, ethylenesulfonic acids, halogenbenzenesulfonic, toluenesulfonic, naphthylsulphonic acids, or sulfanilic acid, methionine, tryptophane, lysine or arginine.

These or other salts of the new compounds such as, e.g., picrates may serve as purifying agents of the free bases obtained as the free bases are transformed into salts, these are separated and the bases are then set free from the salts again. According to the close relationship between the new compounds in free form and in the form of their salts it will be understood from the above and the below that, if possible, the corresponding salts are included when the free compound is mentioned.

The invention also relates to any embodiment of the process in which one starts from any compound obtained as an intermediate in any process step and one carries out the lacking process step, or one breaks off the process at any step, or in which one forms a starting material under the reaction conditions, or in which a reaction component possibly in the form of its salt is present.

Thus, one may react an aldehyde of the formula XIX

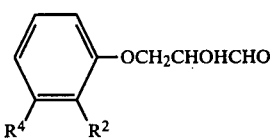

wherein $R^2$ and $R^4$ have the same meaning as given above, and $R^3$ is hydrogen, with an amine of the formula

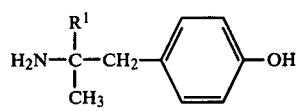

wherein $R^1$ has the same meanings as given above, in the presence of a suitable reducing agent, as one of the above mentioned. Thereby a compound of formula VII is obtained as an intermediate, which then is reduced according to the invention.

Further, one may in a manner known per se react an amine of the formula III with an aldehyde or a ketone of the formula

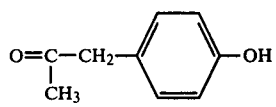

in the presence of a suitable reducing agent, such as one of the above mentioned to produce compounds wherein $R^1$ is hydrogen. Thereby, a compound of formula IX or X is obtained as an intermediate, which then is reduced according to the invention.

The new compounds may, depending on the choice of starting materials and process, be present as optical antipodes or racemate, or, if they contain at least two asymmetric carbon atoms, be present as an isomeric mixture (racemate mixture).

The isomer mixtures (racemate mixtures) obtained may, depending on physical-chemical differences of the component, be separated into both the stereoisomeric (diastereomeric) pure racemate, e.g., by means of chromotography and/or fractional crystallization.

The racemates obtained can be separated according to known methods, e.g., by recrystallization from an optically active solvent, by means of microorganisms, or by reaction with optically active acids forming salts of the compound and separating the salts thus obtained, e.g., by means of their different solubility in the diastereomers, from which the antipodes by the influence of a suitable agent may be set free. Suitably usable optically active acids are, e.g., the L- and D-forms of tartaric acid, di-o-tolyl-tartaric acid, malic acid, mandelic acid, camphersulfonic acid or china acid. Preferably the more active part of the two antipodes is isolated.

Suitably such starting materials are used for carrying out the reactions of the invention, which material leads to groups of end products primarily especially desired and especially to the specifically described and preferred end products.

The starting materials are known or may, if they should be new, be obtained according to processes known per se.

In clinical use the compounds of the invention are administered normally orally, rectally or by injection in the form of a pharmaceutical preparation, which contains an active component either as free base or as a pharmaceutically acceptable, non-toxic acid addition salt, e.g., the hydrochloride, lactate, acetate, sulphamate or the like in combination with a pharmaceutically acceptable carrier.

Mention of the new compounds of the invention herein refers either to the free amine base or the acid addition salts of the free base, even if the compounds are generally or specifically described, provided that the context in which such expressions are used, e.g., in the examples, permits. The carrier may be a solid, semisolid or liquid diluent or a capsule. These pharmaceutical preparations are a further object of the invention. Usually the amount of active compound is between 0.1 to 95% by weight of the preparation, suitably between 0.5 to 20% by weight in preparations for injection and between 2 to 50% by weight in preparations for oral administration.

In the preparation of pharmaceutical compositions containing a compound of the present invention in the form of dosage units for oral administration, the compound elected may be mixed with a solid, pulverulent carrier, as, e.g., with lactose, saccharose, sorbitol, mannitol, starch, such as potato starch, corn starch, amylopectin, cellulose derivatives or gelatine, as well as with an antifriction agent such as magnesium stearate, calcium stearate, polyethyleneglycol waxes or the like, and be pressed into tablets. If coated tablets are wanted, the above prepared core may be coated with a concentrated solution of sugar, which solution may contain, e.g., gum arabic, gelatine, talc, titanium dioxide or the like. Furthermore, the tablets may be coated with a lacquer dissolved in a volatile organic solvent or mixture of solvents. To this coating a dye may be added in order to easily distinguish between tablets with different active compounds or with different amounts of the active compound present.

In the preparation of soft gelatine capsules (pearl-shaped, closed capsules), which consist of gelatine and, e.g., glycerine or in the preparation of similar closed capsules the active compound is mixed with a vegetable oil. Hard gelatine capsules may contain granules of the active compound in combination with a solid, pulverulent carrier such as lactose, saccharose, sorbitol, mannitol, starch (as, e.g., potato starch, corn starch or amylopectin), cellulose derivatives or gelatine.

Dosage units for rectal administration may be prepared in the form of suppositories, which contain the active substance in a mixture with a neutral fat base, or they may be prepared in the form of gelatine-rectal capsules which contain the active substance in a mixture with a vegetable oil or paraffin oil.

Liquid preparations for oral administration may be present in the form of syrups or suspensions, e.g., solutions containing from about 0.2% by weight to about 20% by weight of the active substance described, wherein the residue consists of sugar and a mixture of ethanol, water, glycerol and propylene glycol. If desired, such liquid preparations may contain coloring agents, flavoring agents saccharine and carboxymethylcellulose as a thickening agent.

Solutions for parenteral administration by injection may be prepared as an aqueous solution of a water soluble pharmaceutically acceptable salt of the active compound, preferably in a concentration from about 0.5% by weight to about 10% by weight. These solutions may also contain stabilizing agents and/or buffering agents and may suitably be available in different dosage unit ampoules.

The preparation of pharmaceutical tablets for peroral use is carried out in accordance with the following method:

The solid substances included are ground or sieved to a certain particle size. The binding agent is homogenized and suspended in a certain amount of solvent. The therapeutic compound and necessary auxiliary agents are mixed during a continuous and constant mixing with the binding agent solution and are moistened so that the solution is uniformly divided in the mass without over-moistening any parts. The amount of solvent is usually so adapted that the mass obtains a consistency reminding of wet snow. The moistening of the pulverulent mixture with the binding agent solution causes the particles to gather together slightly to aggregates and the real granulating process is carried out in such a way that the mass is pressed through a sieve in the form of a net of stainless steel having a mesh size of about 1 mm. The mass is then placed in thin layers on a tray to be dried in a drying cabinet. This drying takes place during 10 hours and has to be standardized carefully as the degree of dampness of the granulate is of utmost importance for the following process and for the features of the tablets. Drying in a fluid bed may possibly be used. In this case the mass is not put on a tray but is poured into a container having a net bottom.

After the drying step the granules are sieved so that the desired particle size is obtained. Under certain circumstances powder has to be removed.

To the so-called final mixture, disintegrating, antifriction agents and antiadhesive agents are added. After this mixture the mass should have its right composition for the tabletting step.

The cleaned tablet punching machine is provided with a certain set of punches and dies, whereupon the suitable adjustment for the weight of the tablets and the degree of compression is tested out. The weight of the tablet is decisive for the size of the dose in each tablet and is calculated starting from the amount of therapeutic agent in the granules. The degree of compression affects the size of the tablet, its strength and its ability of disintegrate in water. Especially as regards the two latter properties the choice of compression pressure (0.5 to 5 ton) involves some balancing of conditions. When the right adjustment is set, the preparation of tablets is started which is carried out at a rate of 20,000 to 200,000 tablets per hour. The pressing of the tablets requires different times and depends on the size of the batch.

The tablets are freed from adhering powder in a specific apparatus and are then stored in closed packages until they are delivered.

Many tablets, especially those which are rough or bitter, are coated with a coating. This means that these are coated with a layer of sugar or some other suitable coating.

The tablets are usually packed by machines having an electronic counting device. The different types of packages include glass or plastic gallipots but also boxes, tubes and specific dosage adapted packages may be used.

The daily dose of the active substance varies and is dependent on the type of administration, but as a general rule it is 100 to 400 mg/day of active substance for peroral administration and 5 to 20 mg/day in intravenous administration.

The following illustrates the principle and the adaptation of invention, however, without being limited thereto. Temperature is given in degree Celsius.

EXAMPLE 1

Preparation of 3-[2-(4-hydroxyphenyl)-1-methylethylamino]-1-o-methylphenoxy-propanol-2.

2.5 g or 1,2-epoxy-3-o-methylphenoxy propane were mixed with 1.5 g of 1-(4-hydroxyphenyl)-2-amino-propane and 25 ml of isopropanol and the total solution was refluxed for 1.5 hours. The solution was thereupon evaporated in vacuo. The base thus obtained was dissolved in acetone and the hydrochloride was precipitated using HCl in ether. The hydrochloride was filtered off and washed with acetonitrile. The yield of 3-[2-(4-hydroxyphenyl)-1-methylethylamino]-1-o-methylphenoxypropanol-2 was 1.4 g. Melting point 112° C. The structure was determined using NMR.

EXAMPLE 2

3-[2-(4-hydroxyphenyl)-1-methylethylamino]-1-o-ethylphenoxy-propanol-2 was prepared according to Example 1 using 1,2-epoxy-3-(o-ethyl)phenoxy-propane and 1-(4-hydroxyphenyl)-2-amino-propane as starting materials. Melting point of its hydrochloride is 143° C. Its structure was determined by NMR and equivalent weight.

EXAMPLE 3

3-[2-(4-hydroxyphenyl)-1-methylethylamino]-1-o-allylphenoxy-propanol-2 was prepared according to Example 1 using 1,2-epoxy-3-o-allylphenoxy-propane and 1-(4-hydroxyphenyl)-2-amino-propane as starting material. Melting point of tartrate is 71° C. Its structure was determined by NMR and equivalent weight.

EXAMPLE 4

3-[2-(4-hydroxyphenyl)-1-methylethylamino]-1-o-propargyloxyphenoxy-propanol-2 was prepared according to Example 1 using 1,2-epoxy-3-o-propargyloxyphenoxy-propane and 1-(4-hydroxyphenyl)-2-aminopropane as starting material. The p-hydroxybenzoate was prepared.

EXAMPLE 5

3-[2-(4-hydroxyphenyl)-1,1-dimethylethylamino]-1-o-methylphenoxy-propanol-2 was prepared according to Example 1, using 1,2-epoxy-3-o-methylphenoxypropane and 2-(4-hydroxyphenyl)-1,1-dimethylethyl amine as starting materials. The hydrochloride was obtained as a water soluble oil and its structure was determined using NMR.

EXAMPLE 6

3-[2-(4-hydroxyphenyl)-1,1-dimethylethylamino]-1-o-ethylphenoxy-propanol-2 was prepared according to Example 1 using 1,2-epoxy-3-o-ethylphenoxypropane and 2-(4-hydroxyphenyl)-1,1-dimethylethlamine as starting materials. The melting point of the hydrochloride is 154° C.

EXAMPLE 7

3-[2-(4-hydroxyphenyl)-1,1-dimethylethylamino]-1-o-allylphenoxy-propanol-2 was prepared according to Example 1, using 1,2-epoxy-3-o-allylphenoxypropane and 2-(4-hydroxyphenyl)-1,1-dimethylethylamine as starting materials. The melting point of the hydrochloride is 140° C.

EXAMPLE 8

3-[2-(4-hydroxyphenyl)-1,1-dimethylethylamino]-3-o-propargyloxyphenoxy-propanol-2 was prepared according to Example 1, using 1,2-epoxy-3-o-propargyloxyphenoxypropane and 2-(4-hydroxyphenyl)-1,1-dimethylethylamine as starting materials.

EXAMPLE 9

3-[2-(4-hydroxyphenyl)-1-methylethylamino]-1-[2,3-dimethylphenoxy]-propanol-2 was prepared in accordance with Example 1 using 1,2-epoxy-3-[3,3-dimethylphenoxy]propane and 2-(4-hydroxyphenyl)-1-methylethylamine, as starting materials. Melting point 125° F. (HCl).

EXAMPLE 10

3-[2-(4-hydroxyphenyl)-1-methylethylamino]-1-o-methoxyphenoxy-propanol-2 was prepared in accordance with Example 1 using 1,2-epoxy-3-o-methoxyphenoxy-propane and 2-(4-hydroxyphenyl)-1-methylethylamine as starting materials. Melting point 114° C. (HCl).

EXAMPLE 11

3-methyl-3-[2-(4-hydroxyphenyl)-1-methylethylamino]-1-o-ethylphenoxy-propanol-2 was prepared in accordance with Example 1 using 1,2-epoxy-1-methyl-3-o-ethylphenoxy-propane and 2-(4-hydroxyphenyl)-1-methylethylamine, as starting materials. The hydrochloride was obtained as a water soluble oil and its structure was determined using NMR.

EXAMPLE 12

3-ethyl-3-[2-(4-hydroxyphenyl)-1-methylethylamino]-1-o-allylphenoxy-propanol-2 was prepared in accordance with Example 1 above using 1,2-epoxy-1-ethyl-3-o-allylphenoxy-propanol and 2-(4-hydroxyphenyl)-1-methylethylamine as starting materials. The hydrochloride was obtained as a water soluble oil and its structure was determined using NMR.

EXAMPLE 13

3-methyl-3-[2-(4-hydroxyphenyl)-1,1-dimethylethylamino]-1-o-methylphenoxy-propanol-2 was prepared in accordance with Example 1 above using 1,2-epoxy-1-methyl-3-o-methylphenoxy-propane and 2-(4-hydroxyphenyl)-1,1-dimethylethylamine as starting materials. The hydrochloride was obtained as a water soluble oil and its structure was determined using NMR.

EXAMPLE 14

3-methyl-3-[2-(4-hydroxyphenyl)-1,1-dimethylethylamino]-1-o-allylphenoxy-propanol-2 was prepared in accordance with Example 1 above using 1,2-epoxy-1-methyl-3-o-allylphenoxy-propane and 2-(4-hydroxyphenyl)-1,1-dimethylethylamine as starting materials. Melting point 172° C. (HCl).

EXAMPLE 15

3-[2-(4-hydroxyphenyl)-1-methylethylamino]-1-m-methylphenoxy-propanol-2 was prepared in accordance with Example 1 using 1,2-epoxy-3-m-methylphenoxy-propane and 2-(4-hydroxyphenyl)-1-methylethylamine as starting materials. Melting point 150° C. (HCl).

EXAMPLE 16

3-[2-(4-hydroxyphenyl)-1-methylethylamino]-1-o-propylphenoxy-propanol-2 can be prepared in accordance with Example 1, with appropriate substitution of starting materials. Its melting point as the hydrochloride is 129° C.

EXAMPLE 17

A syrup containing 2% (weight per volume of active substance) was prepared from the following ingredients:

| | |
|---|---|
| 3-[2-(4-hydroxyphenyl)-1-methylethylamino]-1-o-methylphenoxy-propanol-2 HCl | 2.0 g |
| Saccharine | 0.6 g |
| Sugar | 30.0 g |
| Glycerine | 5.0 g |
| Flavoring agent | 0.1 g |
| Ethanol 96% | 10.0 g |
| Distilled water | ad 100.0 ml |

Sugar, saccharine and the ether salt were dissolved in 60 g of warm water. After cooling glycerine and solution of flavoring agents dissolved in ethanol were added. To the mixture water was then added to 100 ml.

The above-given active substance may be replaced with other pharmaceutically acceptable acid addition salts.

EXAMPLE 18

3-[2-(4-hydroxyphenyl)-1,1-dimethylethylamino-1-o-allylphenoxy]-propanol-2 hydrochloride (250 g) was mixed with lactose (175.8 g) potato starch (169.7 g) and colloidal silicic acid (32 g). The mixture was moistened with a 10% solution of gelatine and was granulated through a 12-mesh sieve. After drying potato starch (160 g), talc (50 g) and magnesium stearate (5 g) were admixed and the mixture thus obtained was pressed into tablets (10,000) which contain 25 mg of substance. The tablets are sold on the market provided with a breaking score to give another dose than 25 mg or to give fractionals thereof when broken.

EXAMPLE 19

Granules were prepared from 3-[2-(4-hydroxyphenyl)-1-methylethylamino]-1-o-propargyloxyphenoxy-propanol-2-p-hydroxybenzoate (250 g), lactose (175.9 g) and an alcoholic solution of polyvinylpyrrolidone (25 g). After the drying step the granules were mixed with talc (25 g), potato starch (40 g) and magnesium stearate (2.50 g) and was pressed into 10,000 biconvex tablets. These tablets are primarily coated with a 10% alcoholic solution of shellac and thereupon with an aqueous solution containing saccharose (45%), gum arabicum (5%), gelatine (4%) and dyestuff (0.2%). Talc and powdered sugar were used for powdering after the first five coatings. The coating was then coated with a 66% sugar syrup and polished with a 10% carnauba wax solution in carbon tetrachloride.

EXAMPLE 20

3-[2-(4-hydroxyphenyl)-1,1-dimethylethylamino]-3-o-ethylphenoxy-propanol-2-hydrochloride (1 g), sodium chloride (0.8 g) and ascorbic acid (0.1 g) were dissolved in sufficient amount of distilled water to give 100 ml of solution. This solution, which contains 10 mg of active substance on each ml, was used in filling ampoules, which were sterilized by heating at 120° C. for 20 minutes.

Biological Effects

I. β-blocking activity

Anesthetized cats (males and females weighing 2.5–3.5 kg) were pretreated with reserpine (5 mg/kg bodyweight administered intramuscularly) about 16 hours before the experiments. The animals were pretreated with reserpine in order to eliminate the endogenous sympathetic control of heart rate and vascular smooth muscle tone. The cats were anesthetized with pentobarbital (30 mg/kg bodyweight administered i.p.) and artificially ventilated with room air. A bilateral vagotomy was performed in the neck. Blood pressure was obtained from a cannulated carotid artery and heart rate was registered from a cardiotachometer, triggered by the electrocardiogram (ECG). One female artery was cannulated and perfused with the cat's own blood, delivered at a constant flow rate with a Watson Marlow roller pump. The perfusion pressure was recorded with a Statham pressure transducer. The blood flow rate was so adjusted that the initially recorded perfusion pressure was slightly above the systemic arterial mean blood pressure. In the studied hind limb the paw was excluded from the circulation by a tight ligature. An isoprenaline dose administered intravenously was established giving a submaximal heart rate (HR) increase and a submaximal decrease of peripheral vascular resistance (PR). The latter is shown as a drop of perfusion pressure.

To start the test, an initial dose of the test compound is injected into the animal. Ten minutes afterward the predetermined dose of isoprenaline is injected and the effect of the isoprenaline on the heart rate and peripheral resistance is noted. By comparing these observations with the normal response of the test animal to the predetermined dose of isoprenaline, the percent blockade of the HR and PR caused by the initial dose of test compound is calculated. The experiment is repeated with logrithmically increasing doses of the test compound (on a cumulative basis), alternating with the predetermined dose of isoprenaline every 10 minutes. From these data, a dose-response curve is constructed and the $ED_{50}$ values for HR blockade and PR blockade are estimated.

After the final dose of the test compound is administered—which is sufficient to cause a 100% blockade of the isoprenaline response—the intrinsic activity of the test compound is noted as the increase in heart rate relative to the basal heart rate of the test animal before the experiment began.

II. α-blocking activity

α-blocking activity was tested in isolated rat vas deferens. Rats were decapitated and the vas deferens immediately dissected out and mounted in an oxygenated Krebs Ringer solution at 37° C. Noradrenaline administered to the bath caused α-receptor mediated contraction of vas deferens, which was recorded with an isometric tension transducer. Dose response curves to noradrenaline were constructed before and after three increasing doses of the test compound. By using Schildt plots $pA_2$ values for α-receptor blockade were obtained. By definition $pA_2 = -$log concentration of an antagonist (in this case, the test compound) which requires that the concentration of the related agonist (in this case noradrenaline) be doubled in the presence of the antagonist in order to produce the same effect as the agonist caused in the absence of the antagonist. The calculated $pA_2$- values are given in Table I.

III. Blood pressure lowering effect in conscious dog

Beagle dogs were trained to be lying quietly on a table. Arterial blood pressure was registered via a blood pressure transducer attached to the dog at the heart level which was connected to an implanted catheter in the abdominal aorta. All dogs were pretreated with methylscopolamine to avoid vagal influences. Recordings were taken before and 15 minutes after administration of the test compound. The test compounds were given in successive injections of 0.5 and 1.5 mg/kg i.v. The latter corresponds to a cumulative dose of 2.0 mg/kg.

The effect on blood pressure for some compounds is given in Table I.

In Table I values for propranolol and metoprolol two pure β-blockers are also included.

TABLE 1

| Compound | Reserpinized cat Block of isopren. $ED_{50}$ mg/kg HR | PR | Intrinsic activity beats/min. | Conscious dog Δ BP in mm Hg After i.v. Injection of β Blocking Agent (Cumulative Dose) 0.5 mg/kg | 2.0 mg/kg | $pA_2$ |
|---|---|---|---|---|---|---|
| Propranolol | 0.1 | 0.1 | 0 | * | | — |
| Metoprolol | 0.2 | 4.7 | 0 | * | | — |
| Ex. 1 | 0.07 | 0.07 | +16 | −24 | −31 | 6.8 |
| Ex. 2 | 0.11 | 0.15 | +32 | −17 | −40 | 7.2 |
| Ex. 3 | 0.7 | 1.1 | +33 | −22 | −16 | 7.2 |
| Ex. 4 | 0.12 | 0.35 | +22 | −34 | −41 | 6.6 |
| Ex. 5 | 0.06 | 0.3 | +62 | −17 | −17 | 5.8 |
| Ex. 6 | 0.04 | 0.04 | +38 | | | 6.8 |
| Ex. 7 | 0.09 | 0.06 | +39 | −28 | −43 | 6.4 |
| Ex. 9 | 0.26 | 0.59 | +3 | | | 6.1 |
| Ex. 10 | 0.04 | 0.5 | +40 | | | 6.4 |
| Ex. 11 | 0.3 | 0.5 | +18 | −32 | −50 | 6.2 |
| Ex. 12 | 5.1 | 3.3 | +2 | | | 6.6 |
| Ex. 13 | 1.3 | 8.5 | +9 | | | 6.2 |
| Ex. 14 | 2.5 | 0.6 | +3 | | | 7.4 |
| Ex. 15 | 0.3 | 0.9 | +16 | | | 5.2 |
| Ex. 16 | 1.3 | 0.8 | +35 | | | 6.8 |

*Measured at a dose of 1.5 mg/kg, the effects of propranolol (+5 mm Hg) and metoprolol (−5 mm Hg) were experimentally not significant.

We claim:

1. A compound of the formula I

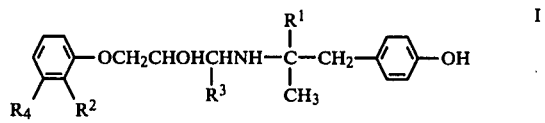

wherein $R^1$ is selected from the group consisting of hydrogen and methyl and $R^2$ is selected from the group consisting of hydrogen, methyl, ethyl, propyl, allyl, methoxy and propargyloxy, $R^3$ is selected from the group consisting of hydrogen, methyl and ethyl, and $R^4$ is selected from the group consisting of hydrogen and methyl, provided that $R^2$ and $R^4$ are not both hydrogen, or a therapeutically acceptable salt of such a compound.

2. A compound according to claim 1 wherein $R^2$ is methyl, ethyl, propyl, allyl, methoxy and propargyloxy.

3. A compound according to claim 2 wherein $R^4$ is hydrogen.

4. A compound according to claim 3 wherein $R^3$ is hydrogen or methyl.

5. A compound according to claim 4 wherein $R^2$ is methyl, ethyl, allyl or propargyloxy.

6. A compound according to claim 1 in the form of a dextro-rotating optical antipode.

7. A compound according to claim 1 in the form of a levo-rotating optical antipode.

8. A compound according to claim 1 in the form of the free base.

9. A compound according to claim 1 in the form of a therapeutically acceptable salt.

10. The compound according to claim 1 which is 3-[2-(4-hydroxyphenyl)-1-methylethylamino]-1-o-methylphenoxy-propanol-2 or a pharmaceutically acceptable salt thereof.

11. The compound according to claim 1 which is 3-[2-(4-hydroxyphenyl)-1-methylethylamino]-1-o-ethylphenoxy-propanol-2, or a pharmaceutically acceptable salt thereof.

12. The compound according to claim 1 which is 3-[1-methyl-2-(4-hydroxyphenyl)ethylamino]-1-o-propylphenoxy-propanol-2, or a pharmaceutically acceptable salt thereof.

13. The compound according to claim 1 which is 3-[2-(4-hydroxyphenyl)-1-methylethylamino]-1-o-allylphenoxy-propanol-2, or a pharmaceutically acceptable salt thereof.

14. The compound according to claim 1 which is 3-[2-(4-hydroxyphenyl)-1-methylethylamino]-1-o-propargyloxyphenoxy-propanol-2, or a pharmaceutically acceptable salt thereof.

15. The compound according to claim 1 which is 3-[2-(4-hydroxyphenyl)-1,1-dimethylethylamino]-1-o-methylphenoxy-propanol-2, or a pharmaceutically acceptable salt thereof.

16. The compound according to claim 1 which is 3-[2-(4-hydroxyphenyl)-1,1-dimethylethylamino]-1-o-ethylphenoxy-propanol-2, or a pharmaceutically acceptable salt thereof.

17. The compound according to claim 1 which is 3-[2-(4-hydroxyphenyl)-1,1-dimethylethylamino]-1-o-propylphenoxy-propanol-2, or a pharmaceutically acceptable salt thereof.

18. The compound according to claim 1 which is 3-[2-(4-hydroxyphenyl)-1,1-dimethylethylamino]-1-o-allylphenoxy-propanol-2, or a pharmaceutically acceptable salt thereof.

19. The compound according to claim 1 which is 3-[2-(4-hydroxyphenyl)-1,1-dimethylethylamino]-1-[o-propargyloxyphenoxy]-propanol-2, or a pharmaceutically acceptable salt thereof.

20. The compound according to claim 1 which is 3-ethyl-3-[1-methyl-2-(4-hydroxyphenyl)ethylamino]-1-o-allylphenoxy-propanol-2, or a pharmaceutically acceptable salt thereof.

21. The compound according to claim 1 which is 3-[2-(4-hydroxyphenyl)-1-methylethylamino]-1-[2,3-dimethylphenoxy]-propanol-2, or a pharmaceutically acceptable salt thereof.

22. The compound according to claim 1 which is 3-[2-(4-hydroxyphenyl)-1-methylethylamino]-1-o-methoxyphenoxy-propanol-2, or a pharmaceutically acceptable salt thereof.

23. The compound according to claim 1 which is 3-methyl-3-[2-(4-hydroxyphenyl)-1-methylethylamino]-1-o-ethylphenoxy-propanol-2, or a pharmaceutically acceptable salt thereof.

24. The compound according to claim 1 which is 3-methyl-3-[2-(4-hydroxyphenyl)-1,1-dimethylethylamino]-1-o-methylphenoxy-propanol-2, or a pharmaceutically acceptable salt thereof.

25. The compound according to claim 1 which is 3-methyl-3-[2-(4-hydroxyphenyl)-1,1-dimethylethylamino]-1-o-allylphenoxy-propanol-2, or a pharmaceutically acceptable salt thereof.

26. The compound according to claim 1 which is 3-[2-(4-hydroxyphenyl)-1-methylethylamino]-1-m-methylphenoxy-propanol-2, or a pharmaceutically acceptable salt thereof.

27. A method of treating cardiovascular disorders by blocking the β-receptors of the heart which comprises administering to mammals in need of said treatment, an amount effective to block said β-receptors of a compound of the general formula I

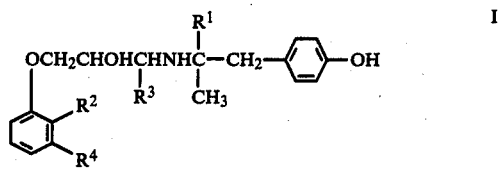

wherein $R^1$ is selected from the group consisting of hydrogen and methyl, and $R^2$ is selected from the group consisting of hydrogen, methyl, ethyl, propyl, allyl, methoxy, propargyloxy, $R^3$ is selected from the group consisting of hydrogen, methyl, and ethyl, and $R^4$ is selected from the group consisting of hydrogen and methyl, provided that $R^2$ and $R^4$ are not both hydrogen, or its therapeutically acceptable acid addition salt.

28. A method according to claim 27 wherein $R^2$ of said compound is methyl, ethyl, propyl, allyl, methoxy, or proparglyloxy.

29. A method according to claim 28 wherein $R^4$ in said compound is hydrogen.

30. A method according to claim 29 wherein $R^3$ in said compound is hydrogen or methyl.

31. A method according to claim 30 wherein $R^2$ in said compound is methyl, ethyl, allyloxy or propargyloxy.

32. A method according to claim 27 wherein said compound is 3-[2-(4-hydroxyphenyl)-1-methylethylamino]-1-o-methylphenoxy-propanol-2, or a pharmaceutically acceptable salt thereof.

33. A method according to claim 27 wherein said compound is 3-[2-(4-hydroxyphenyl)-1-methylethylamino]-1-o-ethylphenoxy-propanol-2, or a pharmaceutically acceptable salt thereof.

34. A method according to claim 27 wherein said compound is 3-[1-methyl-2-(4-hydroxyphenyl)ethylamino]-1-o-propylphenoxy-propanol-2, or a pharmaceutically acceptable salt thereof.

35. A method according to claim 27 wherein said compound is 3-[2-(4-hydroxyphenyl)-1-methylethylamino]-1-o-allylphenoxy-propanol-2, or a pharmaceutically acceptable salt thereof.

36. A method according to claim 27 wherein said compound is 3-[2-(4-hydroxyphenyl)-1-methylethylamino]-1-o-propargyloxyphenoxy-propanol-2, or a pharmaceutically acceptable salt thereof.

37. A method according to claim 27 wherein said compound is 3-[2-(4-hydroxyphenyl)-1,1-dimethylethylamino]-1-o-methylphenoxy-propanol-2, or a pharmaceutically acceptable salt thereof.

38. A method according to claim 27 wherein said compound is 3-[2-(4-hydroxyphenyl)-1,1-dimethylethylamino]-1-o-ethylphenoxy-propanol-2, or a pharmaceutically acceptable salt thereof.

39. A method according to claim 27 wherein said compound is 3-[2-(4-hydroxyphenyl)-1,1-dimethylethylamino]-1-o-propylphenoxy-propanol-2, or a pharmaceutically acceptable salt thereof.

40. A method according to claim 27 wherein said compound is 3-[2-(4-hydroxyphenyl)-1,1-dimethylethylamino]-1-o-allylphenoxy-propanol-2, or a pharmaceutically acceptable salt thereof.

41. A method according to claim 27 wherein said compound is 3-[2-(4-hydroxyphenyl)-1,1-dimethylethylamino]-3-o-propargyloxyphenoxy-propanol-2, or a pharmaceutically acceptable salt thereof.

42. A method according to claim 27 wherein said compound is 3-ethyl-3-[1-methyl-2-(4-hydroxyphenyl)ethylamino]-1-o-allylphenoxy-propanol-2, or a pharmaceutically acceptable salt thereof.

43. A method according to claim 27 wherein said compound is 3-[2-(4-hydroxyphenyl)-1-methylethylamino]-1-(2,3-dimethylphenoxy)-propanol-2, or a pharmaceutically acceptable salt thereof.

44. A method according to claim 27 wherein said compound is 3-[2-(4-hydroxyphenyl)-1-methylethylamino]-1-o-methoxyphenoxy-propanol-2, or a pharmaceutically acceptable salt thereof.

45. A method according to claim 27 wherein said compound is 3-methyl-3-[2-(4-hydroxyphenyl)-1-methylethylamino]-1-o-ethylphenoxy-propanol-2, or a pharmaceutically acceptable salt thereof.

46. A method according to claim 27 wherein said compound is 3-methyl-3-[2-(4-hydroxyphenyl)-1,1-dimethylethylamino]-1-o-methylphenoxy-propanol-2, or a pharmaceutically acceptable salt thereof.

47. A method according to claim 27 wherein said compound is 3-methyl-3-[2-(4-hydroxyphenyl)-1,1-dimethylethylamino]-1-o-allylphenoxy-propanol-2, or a pharmaceutically acceptable salt thereof.

48. A method according to claim 27 wherein said compound is 3-[2-(4-hydoxyphenyl)-1-methylethylamino]-1-m-methylphenoxy-propanol-2, or a pharmaceutically acceptable salt thereof.

49. A pharmaceutical composition for the treatment of cardiovascular disorders which comprises as an active ingredient a therapeutically effective dose of at least one $\beta$-receptor blocking phenoxy hydroxy propylamine compound of the formula

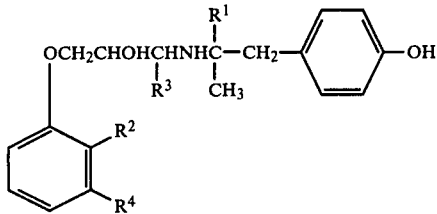

wherein $R^1$ is selected from the group consisting of hydrogen and methyl and $R^2$ is selected from the group consisting of hydrogen, methyl, ethyl, propyl, allyl, methoxy, and propargyloxy, $R^3$ is selected from the group consisting of hydrogen, methyl, and ethyl, and $R^4$ is selected from the group consisting of hydrogen and methyl, provided that $R^2$ and $R^4$ are not both hydrogen, in association with a pharmaceutically acceptable carrier.

50. A pharmaceutical composition according to claim 49 wherein $R^2$ in said compound is methyl, ethyl, propyl, allyl, methoxy or propargyloxy.

51. A pharmaceutical composition according to claim 50 wherein $R^4$ in said compound is hydrogen.

52. A pharmaceutical composition according to claim 51 wherein $R^3$ in said compound is hydrogen or methyl.

53. A pharmaceutical composition according to claim 52 wherein $R^2$ in said compound is methyl, ethyl, allyloxy or propargyloxy.

54. A pharmaceutical composition according to claim 49, wherein the active ingredient is a therapeutically effective dose of at least one said compounds in racemic form.

55. A pharmaceutical composition according to claim 49, wherein the active ingredient is a therapeutically effective dose of at least one said compounds as the optically active, dextro-rotatary isomer.

56. A pharmaceutical composition according to claim 49, wherein the active ingredient is a therapeutically effective dose of at least one said compounds as the optically active, levo-rotatary isomer.

57. A pharmaceutical composition according to claim 50, wherein the ortho-substituted phenoxyhydroxypropylamine compound comprises 0.1 to 95% by weight of the preparation.

58. A pharmaceutical composition according to claim 50, in a form suitable for administration by injection wherein the ortho-substituted phenoxyhydroxypropylamine compound comprises about 0.5% to about 20% by weight of the preparation.

59. A pharmaceutical composition according to claim 58 for parenteral application which comprises an aqueous solution of a water soluble salt of said ortho-substituted phenoxyhydroxypropylamine compound in an amount of about 0.5–10% by weight of the preparation.

60. A pharmaceutical composition according to claim 50 in a form suitable for oral administration wherein the ortho-substituted phenoxyhydroxypropylamine compound comprises about 0.2% to about 50% by weight of the preparation.

61. A pharmaceutical composition according to claim 49 wherein the active ingredient is 3-[2-(4-hydroxyphenyl)-1-methylethylamino)-1-o-methylphenoxy]-propanol-2, or a pharmaceutically acceptable non-toxic addition salt thereof.

62. A pharmaceutical composition according to claim 49 wherein the active ingredient is 3-[2-(4-hydroxyphenyl)-1-methylethylamino]-1-o-ethylphenoxy-propanol-2, or a pharmaceutically acceptable non-toxic addition salt thereof.

63. A pharmaceutical composition according to claim 49 wherein the active ingredient is 3-[2-(4-hydroxyphenyl)-1-methylethylamino]-1-o-allylphenoxy-propanol-2, or a pharmaceutically acceptable non-toxic addition salt thereof.

64. A pharmaceutical composition according to claim 49 wherein the active ingredient is 3-[2-(4-hydroxyphenyl)-1-methylethylamino]-1-o-propargyloxyphenoxy-propanol-2, or a pharmaceutically acceptable non-toxic addition salt thereof.

65. A pharmaceutical composition according to claim 49 wherein the active ingredient is 3-[2-(4-hydroxyphenyl)-1,1-dimethylethylamino]-1-o-methylphenoxy-propanol-2, or a pharmaceutically acceptable non-toxic addition salt thereof.

66. A pharmaceutical composition according to claim 49 wherein the active ingredient is 3-[2-(4-hydroxyphenyl)-1,1-dimethylethylamino]-1-o-ethylphenoxy-propanol-2, or a pharmaceutically acceptable non-toxic addition salt thereof.

67. A pharmaceutical composition according to claim 49 wherein the active ingredient is 3-[2-(4-hydroxyphenyl)-1,1-dimethylethylamino]-1-o-allylphenoxy-propanol-2, or a pharmaceutically acceptable non-toxic addition salt thereof.

68. A pharmaceutical composition according to claim 49 wherein the active ingredient is 3-[2-(4-hydroxyphenyl)-1,1-dimethylethylamino]-1-o-propargyloxyphenoxy-propanol-2, or a pharmaceutically acceptable non-toxic addition salt thereof.

69. A pharmaceutical composition according to claim 49 wherein the active ingredient is 3-[2-(4-hydroxyphenyl)-1-methylethylamino]-1-[2,3-dimethylphenoxy]-propanol-2, or a pharmaceutically acceptable non-toxic addition salt thereof.

70. A pharmaceutical composition according to claim 49 wherein the active ingredient is 3-[2-(4-hydroxyphenyl)-1-methylethylamino]-1-o-methoxyphenoxy-propanol-2, or a pharmaceutically acceptable non-toxic addition salt thereof.

71. A pharmaceutical composition according to claim 49 wherein the active ingredient is 3-methyl-3-[2-(4-hydroxyphenyl)-1-methylethylamino]-1-o-ethyl-phenoxy-propanol-2, or a pharmaceutically acceptable non-toxic addition salt thereof.

72. A pharmaceutical composition according to claim 49 wherein the active ingredient is 3-methyl-3-[2-(4-hydroxyphenyl)-1,1-dimethylethylamino]-1-o-methyl-phenoxy-propanol-2 or a pharmaceutically acceptable non-toxic addition salt thereof.

73. A pharmaceutical composition according to claim 49 wherein the active ingredient is 3-methyl-3-[2-(4-hydroxyphenyl)-1,1-dimethylamino]-1-o-allylphenoxy-propanol-2 or a pharmaceutically acceptable non-toxic addition salt thereof.

74. A pharmaceutical composition according to claim 49 wherein the active ingredient is 3-ethyl-3-[2-(4-hydroxyphenyl)-1-methylethylamino]-1-o-allyl-phenoxy-propanol-2, or a pharmaceutically acceptable non-toxic addition salt thereof.

* * * * *

UNITED STATES PATENT AND TRADEMARK OFFICE
CERTIFICATE OF CORRECTION

PATENT NO. : 4,161,542
DATED : July 17, 1979
INVENTOR(S) : Carlsson et al.

It is certified that error appears in the above-identified patent and that said Letters Patent are hereby corrected as shown below:

Col. 20, line 14, "preparation" should read --composition--;

Col. 20, line 19, "preparation" should read --composition--;

Col. 20, line 24, "preparation" should read --composition--;

Col. 20, line 29, "preparation" should read --composition--.

Signed and Sealed this

Seventeenth Day of June 1980

[SEAL]

Attest:

SIDNEY A. DIAMOND

Attesting Officer

Commissioner of Patents and Trademarks